(12) United States Patent
Lu et al.

(10) Patent No.: US 11,752,239 B2
(45) Date of Patent: Sep. 12, 2023

(54) COMBINATION BIOACTIVE SILICATE MEDICINE CARRIER AND SHUNT

(71) Applicants: Luke Lu, San Diego, CA (US); Hsiao Sen Tseng, Taichung (TW); Michelle Lu, San Diego, CA (US); Emily Lu, San Diego, CA (US)

(72) Inventors: Luke Lu, San Diego, CA (US); Hsiao Sen Tseng, Taichung (TW); Michelle Lu, San Diego, CA (US); Emily Lu, San Diego, CA (US)

(73) Assignee: TAIWAN FIBER OPTICS, INC., Taipei (TW)

( * ) Notice: Subject to any disclaimer, the term of this patent is extended or adjusted under 35 U.S.C. 154(b) by 308 days.

(21) Appl. No.: 16/816,579

(22) Filed: Mar. 12, 2020

(65) Prior Publication Data

US 2021/0283316 A1    Sep. 16, 2021

(51) Int. Cl.
| | |
|---|---|
| *A61L 31/02* | (2006.01) |
| *A61F 9/00* | (2006.01) |
| *A61F 9/007* | (2006.01) |
| *A61M 27/00* | (2006.01) |
| *A61L 31/16* | (2006.01) |
| *A61L 31/14* | (2006.01) |

(52) U.S. Cl.
CPC .......... *A61L 31/026* (2013.01); *A61F 9/0017* (2013.01); *A61F 9/00781* (2013.01); *A61L 31/148* (2013.01); *A61L 31/16* (2013.01); *A61M 27/002* (2013.01); *A61F 2250/0067* (2013.01); *A61L 2430/16* (2013.01)

(58) Field of Classification Search
CPC ...... A61L 31/026; A61L 31/148; A61L 31/16; A61L 2430/16; A61F 9/0017; A61F 9/00781; A61F 2250/0067; A61F 2002/068; A61F 2210/0004; A61F 2230/0067; A61F 2250/0068; A61M 27/002; A61M 5/141; A61M 2206/22; A61M 2206/20; A61B 2017/00004
See application file for complete search history.

(56) References Cited

U.S. PATENT DOCUMENTS

| | | | | |
|---|---|---|---|---|
| 2008/0161741 | A1* | 7/2008 | Bene | .............. A61F 9/00781 604/9 |
| 2009/0220612 | A1* | 9/2009 | Perera | ............... B01D 71/48 424/497 |
| 2009/0326483 | A1* | 12/2009 | Green | ............. A61M 25/0017 604/247 |
| 2011/0045055 | A1* | 2/2011 | Hingston | ............ A61L 31/146 424/424 |
| 2015/0182670 | A1* | 7/2015 | Rizk | ................. B29C 43/28 428/221 |
| 2015/0342875 | A1* | 12/2015 | Haffner | ............ A61F 9/0017 53/421 |

* cited by examiner

*Primary Examiner* — Kai H Weng
*Assistant Examiner* — Brandon W. Levy

(57) ABSTRACT

A combination bioactive silicate (e.g., bioactive glass) medicine carrier and shunt of one embodiment includes a shunt which is a tubular member made of bioactive silicate or glass being adapted to be bioresorbable and water soluble, or fiber bundle, the shunt including an insertion end at a first end. Gaps in the bioactive silicate or gaps in the glass adapted to be bioresorbable and water soluble are served as at least one storage for storing medicines.

6 Claims, 9 Drawing Sheets

COMBINATION BIOACTIVE SILICATE MEDICINE CARRIER AND SHUNT

BACKGROUND OF THE INVENTION

1. Field of the Invention

The invention relates to shunts and more particularly to a combination bioactive silicate (e.g., bioactive glass) medicine carrier and shunt, the shunt being adapted to serve as a support of an eyeball, a stent of a blood vessel, or the like so as to lessen transplant rejection, the shunt being adapted to be bioresorbable in a predetermined period of time so as to solve problems of the transplanted tissue rejection and side effect, and the shunt being adapted to direct flow and store medicine.

2. Description of Related Art

Conventionally, after inserting a stent into the lumen of an anatomic vessel of a patient, the patient is required to swallow anti-inflammatory drugs or anti-scarring drugs to less transplant rejection. A large amount of medicine may be dissolved in blood which may circulate through blood vessels to heal a wound because the medicine is swallowed. However, the stent has a probability of 5-10% being blocked annually. Thus, replacement of the stent by operation is required. Unfortunately, there is risk in the operation.

Thus, the need for increasing the performance of an inserted stent in healing a wound exists.

SUMMARY OF THE INVENTION

It is therefore one object of the invention to provide a combination bioactive silicate (e.g., bioactive glass) medicine carrier and shunt comprising a shunt which is a micro capillary member made of bioactive silicate (e.g., bioactive glass) or glass being adapted to be bioresorbable and water soluble, or fiber bundle, the shunt including an insertion end at a first end; wherein gaps in the bioactive silicate fibers (e.g., bioactive glass fibers) or gaps in the glass adapted to be bioresorbable and water soluble are served as at least one storage for storing medicines.

It is another object of the invention to provide a combination bioactive silicate (e.g., bioactive glass) medicine carrier and shunt comprising a shunt which is a micro capillary member made of bioactive silicate or glass being adapted to be bioresorbable and water soluble, or fiber bundle, the shunt including at least one direction check member disposed on an outer surface, an axial channel, and a tapered insertion end at a first end; wherein gaps in the bioactive silicate (e.g., bioactive glass) or gaps in the glass adapted to be bioresorbable and water soluble are served as a plurality of medicine storages for storing medicines.

The invention has the following advantages and benefits in comparison with the conventional art: The shunt is made of bioactive silicate (e.g., bioactive glass) or glass being adapted to be bioresorbable and water soluble. After the shunt has been inserted into the human body, it is capable of minimizing transplant rejection. Further, the shunt can control amount of medicine dissolved in the human body as time evolves. Furthermore, different parts of the shunt are degraded as time evolves so that a desired effect can be carried out by effectively controlling time of discharging medicine. In addition, one or more kinds of medicine can be stored in the medicine storages. After the shunt has been inserted into a predetermined position of the human body, a small amount of medicine is sufficient to heal a wound since the medicine is discharged at a position proximate the location of the wound (or a target).

The above and other objects, features and advantages of the invention will become apparent from the following detailed description taken with the accompanying drawings.

DETAILED DESCRIPTION OF THE INVENTION

Figure 1:
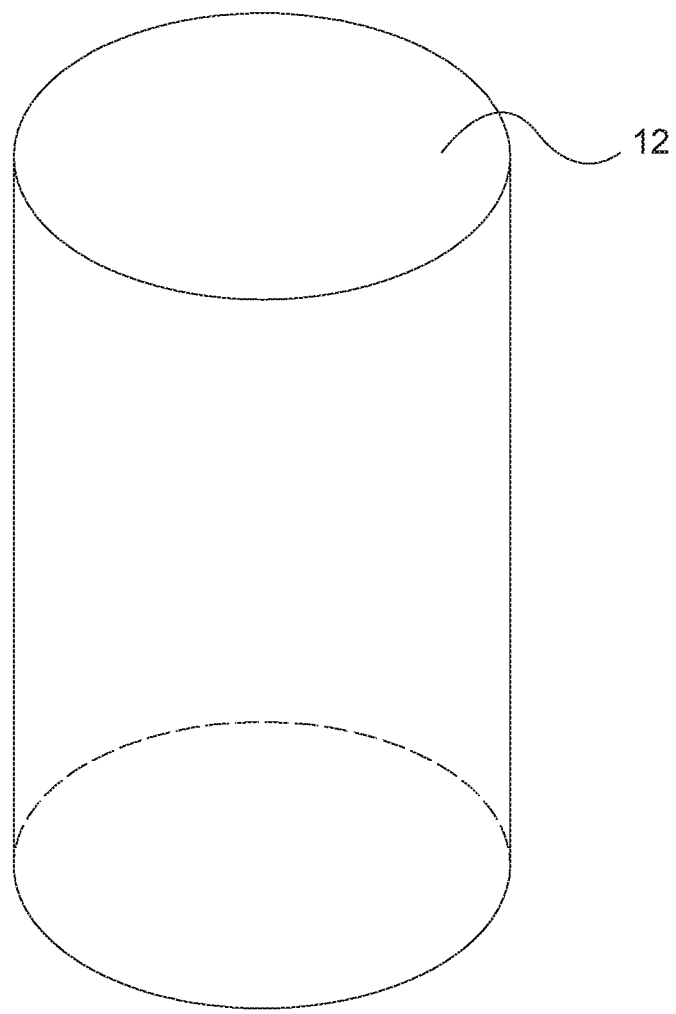
FIG. 1 is a perspective view of a shunt according to a first preferred embodiment of the invention.

Referring to FIG. 1, a combination bioactive silicate (e.g., bioactive glass) medicine carrier and shunt in accordance with a first preferred embodiment of the invention is shown. The combination bioactive silicate (e.g., bioactive glass) medicine carrier and shunt comprises a shunt 10 which is a micro capillary member made of bioactive silicate (e.g., bioactive glass) or glass being adapted to be bioresorbable and water soluble, or fiber bundle. The shunt 10 includes an insertion end 12 at one end. Gaps in the bioactive silicate (e.g., bioactive glass) or gaps in the glass adapted to be bioresorbable and water soluble are served as at least one storage (not shown) for storing medicines.

Figure 2:
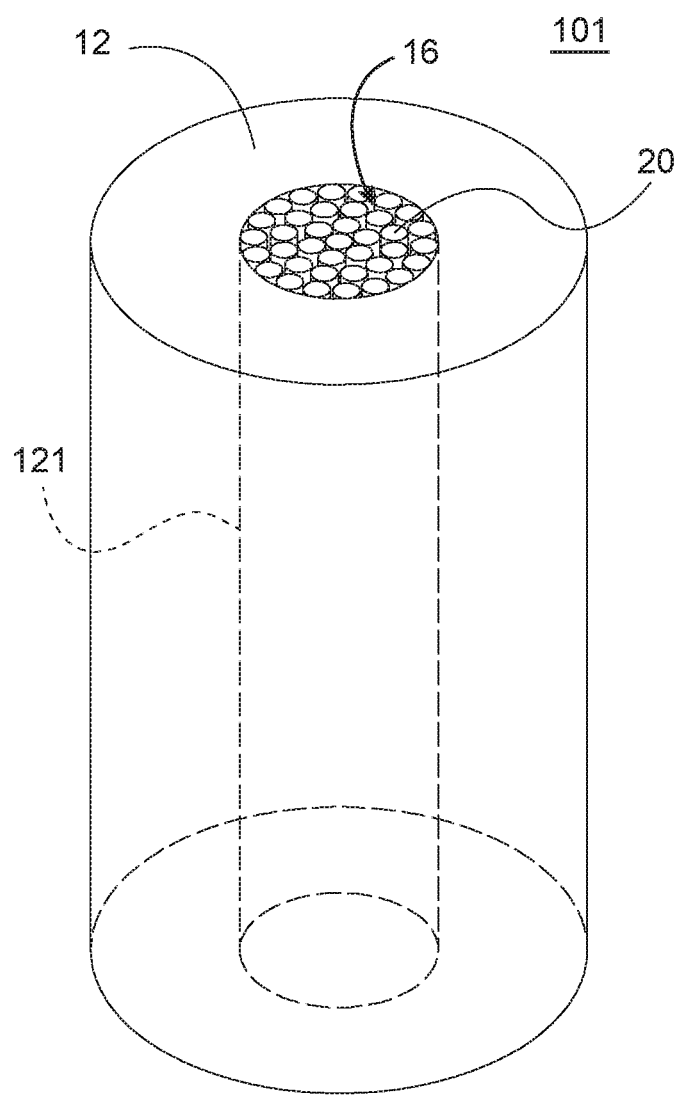
FIG. 2 is a perspective view of a shunt according to a second preferred embodiment of the invention showing fiber bundle disposed through an axial channel.

Referring to FIG. 2, a combination bioactive silicate (e.g., bioactive glass) medicine carrier and shunt in accordance with a second preferred embodiment of the invention is shown. The characteristics of the second preferred embodiment are substantially the same as that of the first preferred embodiment except the following: A plurality of fiber bundle 20 are provided through an axial channel 121 of a fiber bundle shunt 101. A gap among the fiber bundle 20 is defined as a medicine storage 16 for storing medicine. After the fiber bundle shunt 101 has been inserted into a predetermined position of the body, a small amount of medicine is sufficient to heal a wound since the medicine is discharged at a position proximate the location of the wound (or a target).

Figure 3:
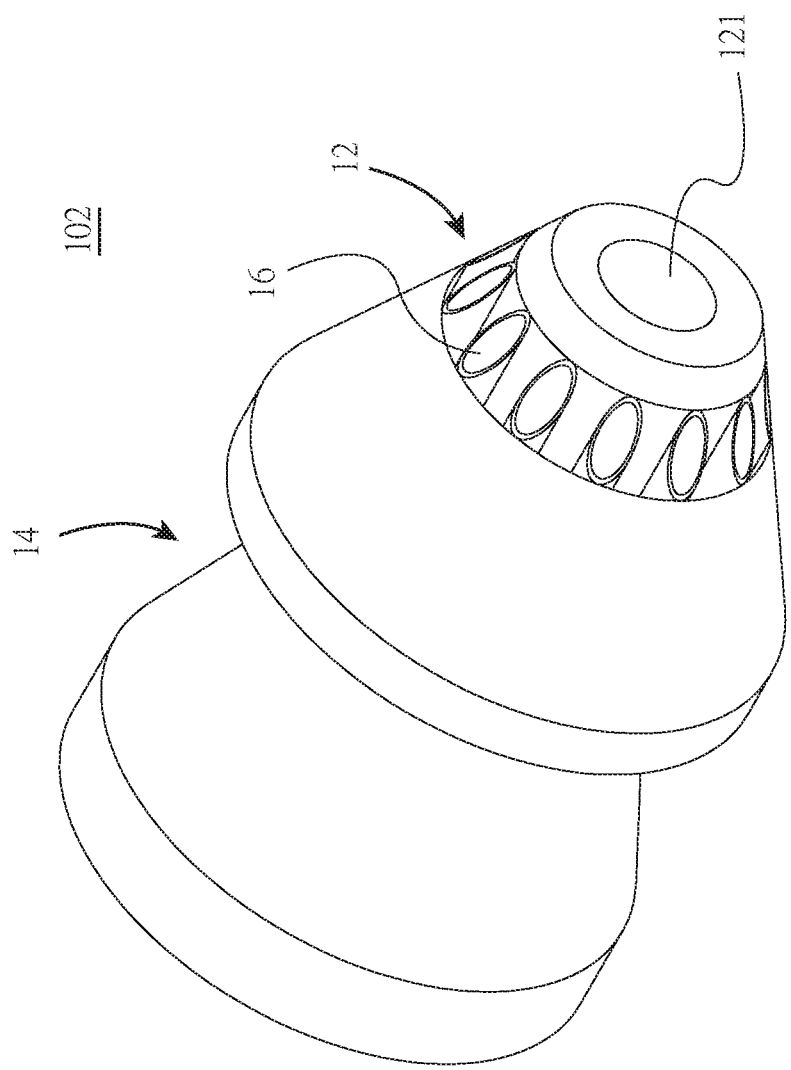
FIG. 3 is a perspective view of a shunt according to a third preferred embodiment of the invention showing a tapered insertion end and a direction check member.
Figure 4:
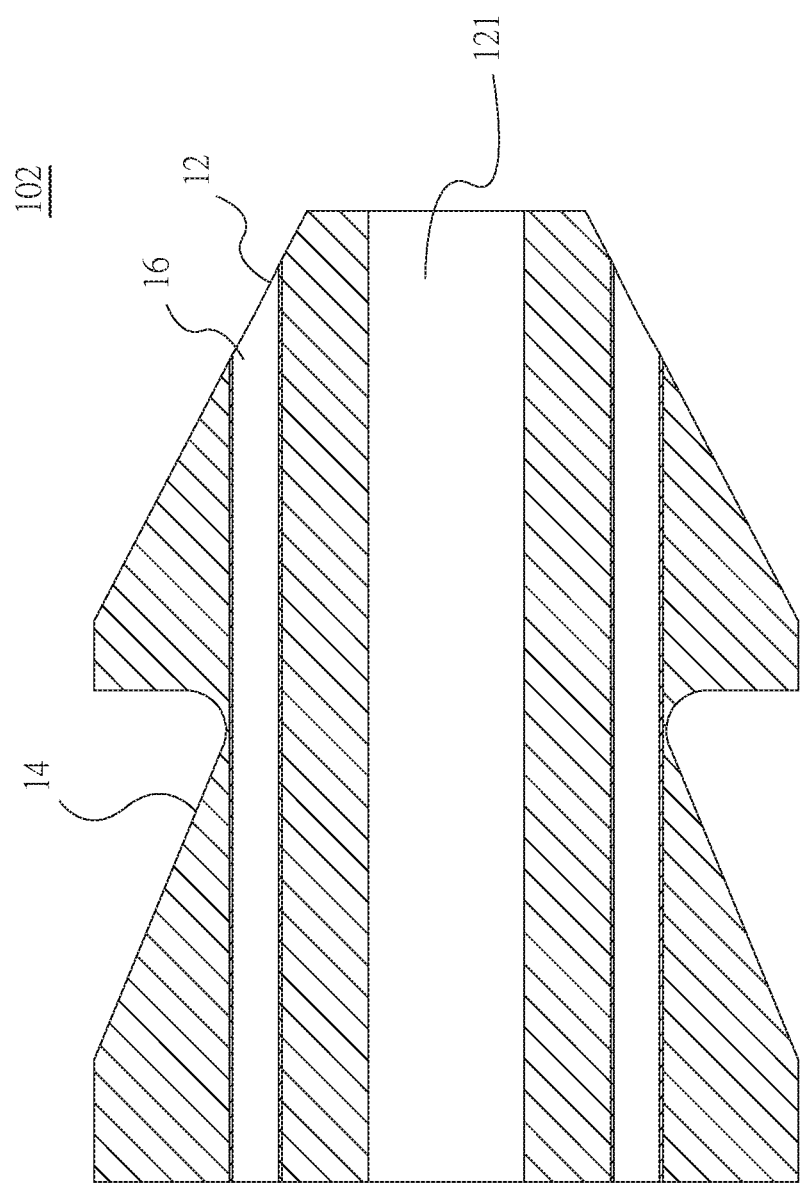
FIG. 4 is a longitudinal sectional view of FIG. 3.
Figure 6:
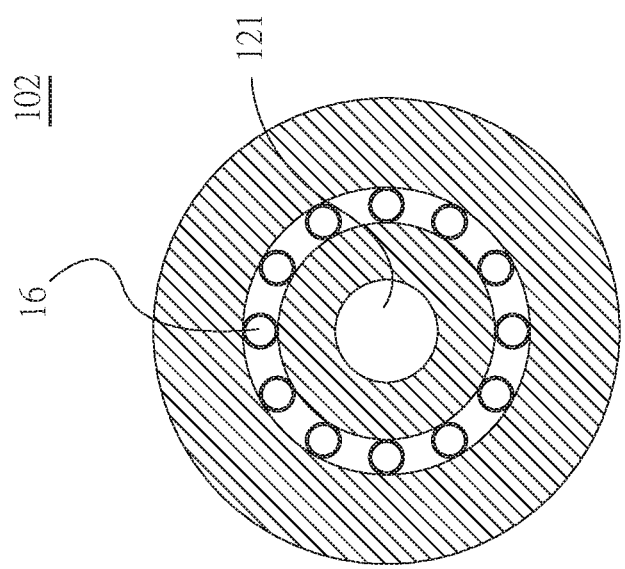
FIG. 6 is a sectional view taken along line 6-6 of FIG. 5.
Figure 5:
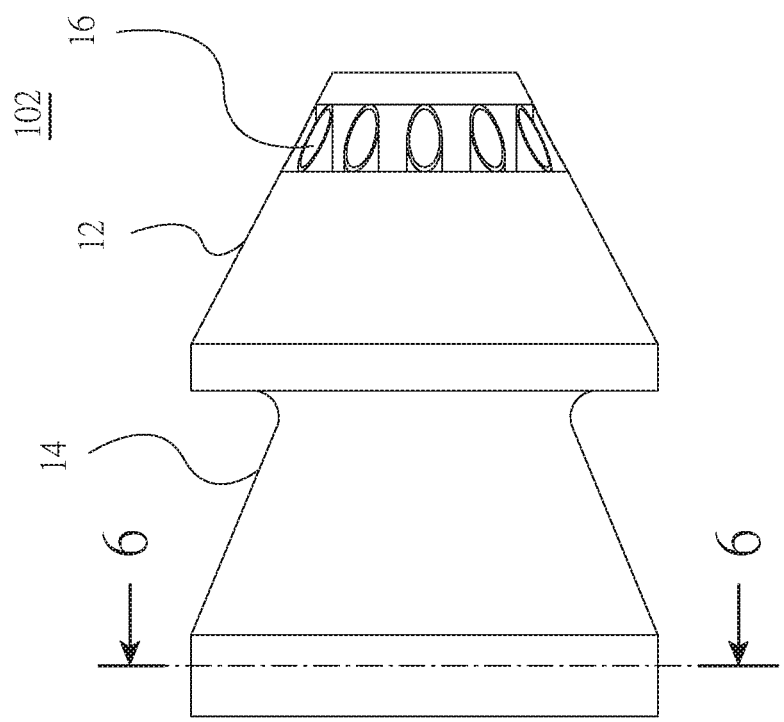
FIG. 5 is a side elevation of FIG. 3.

Referring to FIGS. 3 to 6, a combination bioactive silicate (e.g., bioactive glass) medicine carrier and shunt in accordance with a third preferred embodiment of the invention is shown and comprises a bullet shaped, capsule shaped, or olive shaped shunt 102 which is a capillary member made of bioactive silicate (e.g., bioactive glass) or glass being adapted to be bioresorbable and water soluble, or fiber bundle. The shunt 102 includes a plurality of tunnel shaped medicine storages 16 equally spaced around an axial channel 121. The medicine storages 16 are used to store medicines such as anti-inflammatory drugs, anti-scarring drugs, anti-cancer drugs, or cell-activating drugs. Alternatively, the medicine storages 16 are used to direct flow if there is no medicine stored therein. The axial channel 121 is used to direct flow or store medicine. At least one direction check member 14 is provided on an outer surface of the shunt 102 and is adapted to prevent the shunt 102 from moving toward the insertion direction. Thus, the shunt 102 is stably disposed in a predetermined position. One end of the shunt 102 is formed as a tapered insertion end 12 so as to facilitate the shunt 102 to insert into the predetermined position. As shown in FIG. 3, the direction check member 14 is a portion of an outer wall of shunt 102 behind the tapered insertion end 12 that extends toward the medicine storages 16.

Figure 7:
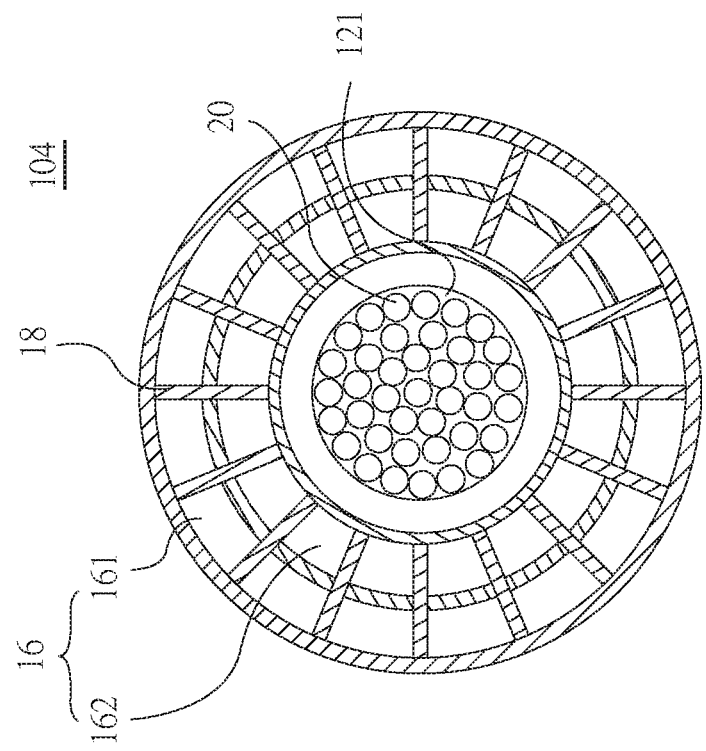
FIG. 7 is a cross-sectional view of a shunt according to a fourth preferred embodiment of the invention.

Referring to FIG. 7, a distributor 103 in accordance with a fourth preferred embodiment of the invention is shown. Each of a plurality of medicine storages 16 of the distributor 103 includes at least one outer space 161 and at least one inner space 162. Medicine stored in the outer space 161 and the inner space 162 can be the same or different. A plurality of dividing members 18 are provided and each dividing member 18 is provided between any two adjacent ones of the outer space 161 and the inner space 162.

Thus, the medicine can be divided. The medicine storages 16 are arranged in a predetermined order rather than being coral shaped or irregular hole shaped. Alternatively, the medicine storages 16 have different thicknesses and are arranged in a predetermined order. As shown in FIG. 7, thicknesses of the dividing members 18 can be the same or different so as to take advantage of different biodegrading speeds to control time and amount of medicine being discharged. In the embodiment, the dividing members 18 are arranged in an order of being thick, thin, thick, thin, etc.

Figure 8:
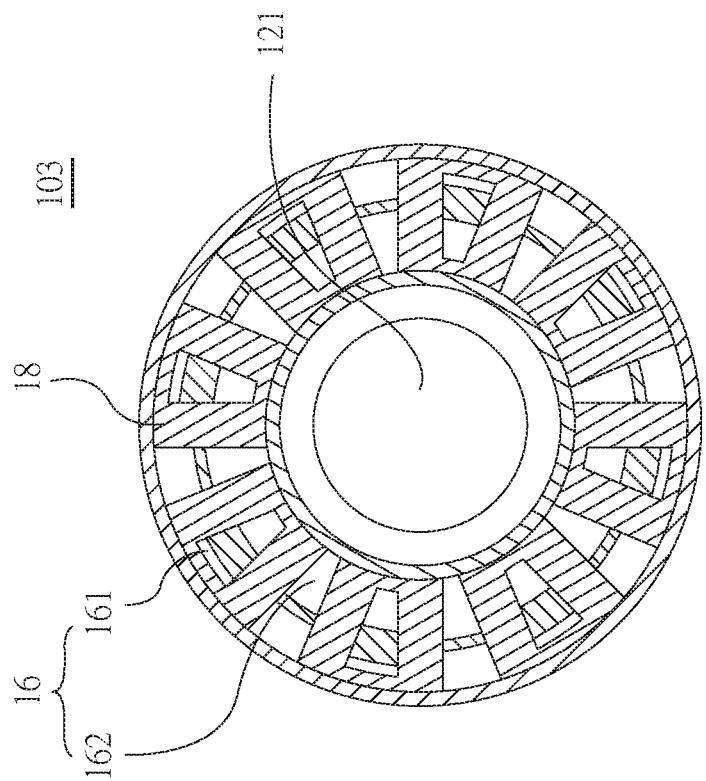
FIG. 8 is a cross-sectional view of a shunt according to a fifth preferred embodiment of the invention.

Referring to FIG. 8, a distributor 104 in accordance with a fifth preferred embodiment of the invention is shown and includes a plurality of axial hollow fiber strands 20 made of bioactive silicate. The fiber strands 20 have a very small diameter. Thus, high pressure fluid at one end of the distributor 104 may flow to the low pressure other end thereof through the fiber strands 20 due to capillary action of the fiber bundle 20. The flow will stop when pressures at two ends of the distributor 104 are equal.

Figure 10:
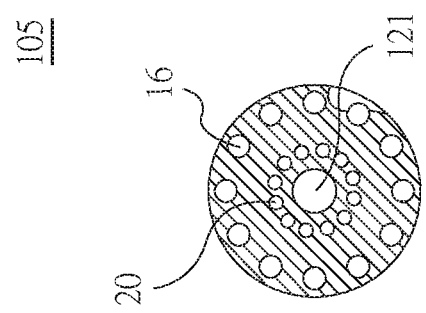
FIG. 10 is a sectional view taken along line 10-10 of FIG. 9.
Figure 9:
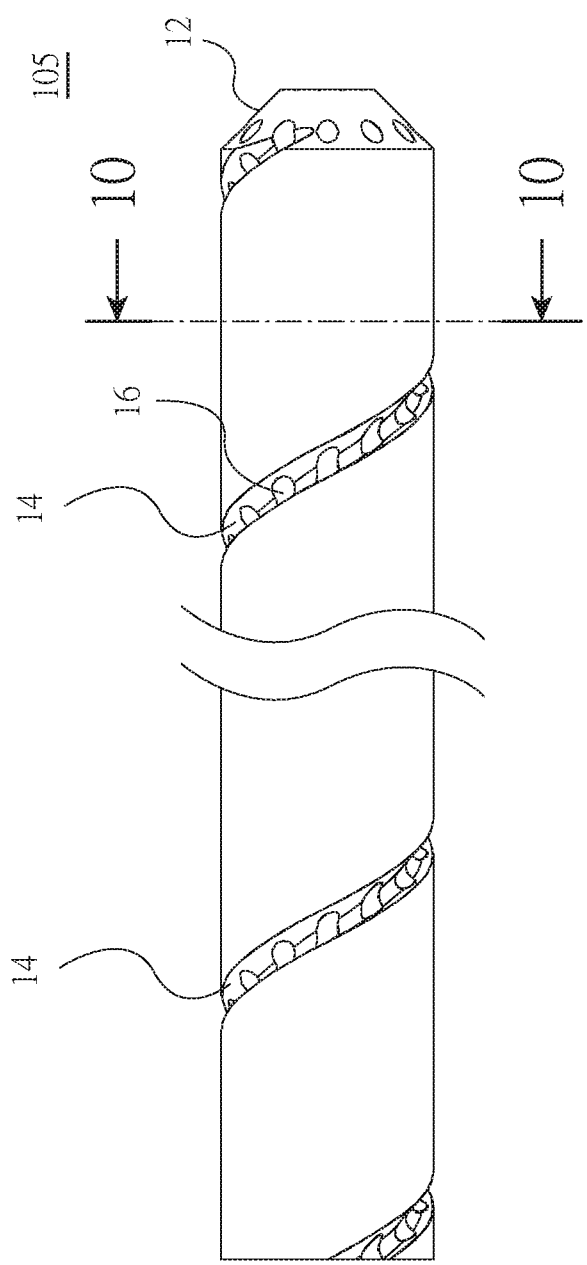
FIG. 9 is a side elevation of a shunt according to a sixth preferred embodiment of the invention.

Referring to FIGS. 9 and 10, a shunt 105 in accordance with a sixth preferred embodiment of the invention is shown and includes a plurality of tunnel shaped parallel medicine storages 16 open to an insertion end 12 at one end. The medicine storage 16 has a circular cross-section. The shunt 105 further comprises a plurality of groove shaped direction check members 14 on an intermediate portion of an outer surface of the distributor 105 for increasing positioning and performance of the distributor 105.

Figure 11:
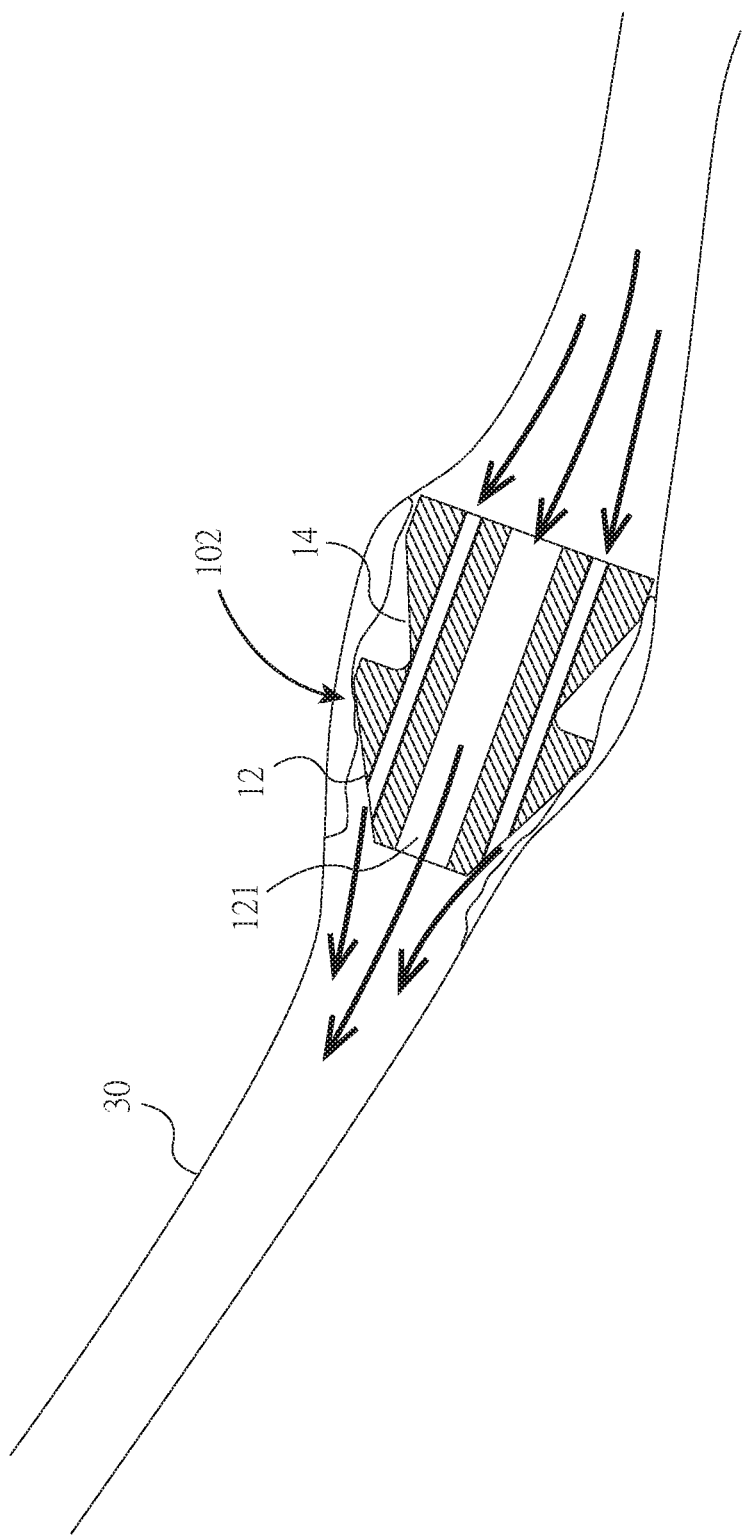
FIG. 11 schematically depicts the shunt of the third preferred embodiment inserted into a blood vessel as support.

Referring to FIG. 11 in conjunction with FIGS. 3 to 6, the shunt 102 is inserted into a blood vessel 30 as support. Further, blood may flow from one end of the shunt 102 to the other end thereof through the channel 121 (or the medicine storages 16). While not shown, the medicine storages 16 are adapted to store medicine such as anti-inflammatory drugs, anti-scarring drugs, anti-cancer drugs, or cell-activating drugs. After the shunt 102 has been inserted into a predetermined position of the blood vessel, a small amount of medicine is sufficient to heal a wound since it is possible of directly discharging the medicine in the blood vessel proximate the location of the wound (or a target).

Figure 13:
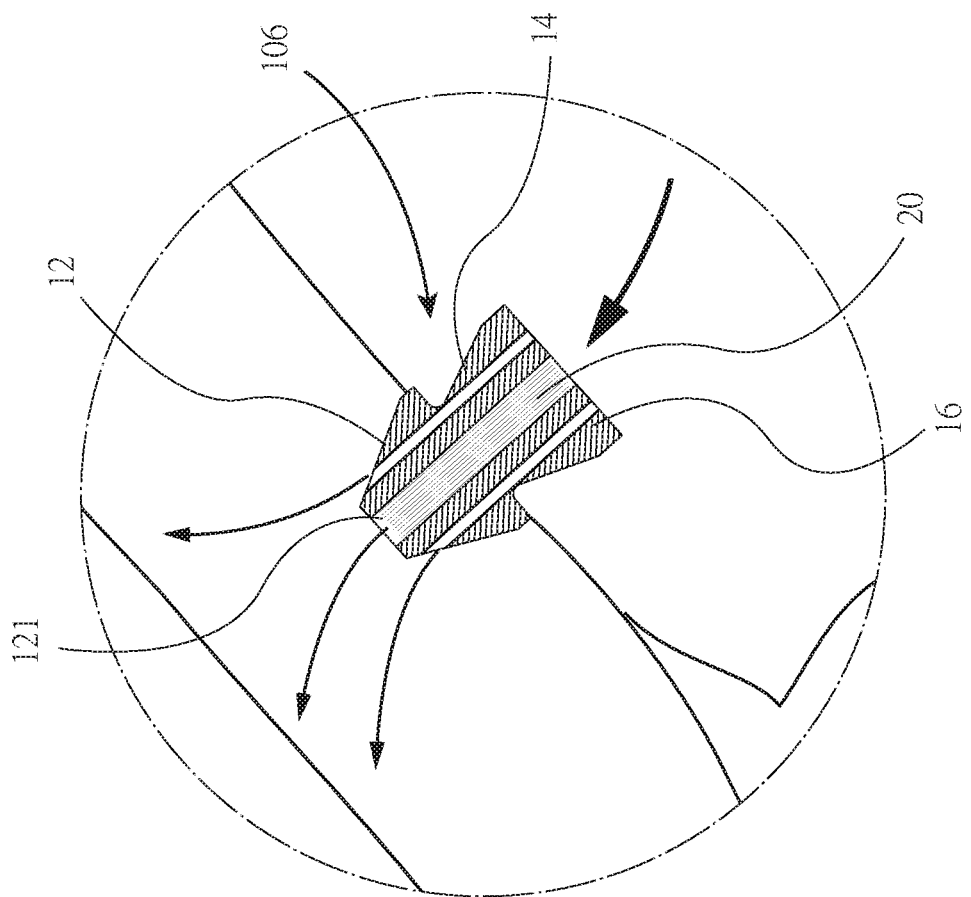
FIG. 13 is a detailed view of a circle of FIG. 12.
Figure 12:
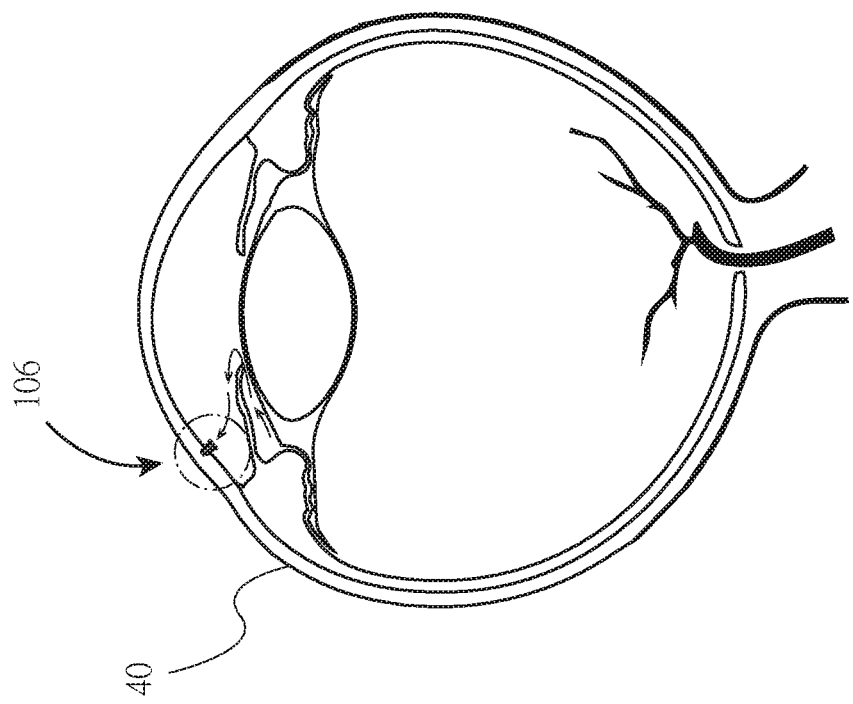
FIG. 12 schematically depicts a shunt according to a seventh preferred embodiment of the invention provided in an eyeball for draining high pressure fluid.

Referring to FIGS. 12 and 13 in conjunction with FIGS. 3 to 6, a shunt 106 in accordance with a seventh preferred embodiment of the invention is shown. The shunt 106 is provided in an inner surface of an eyeball 40. The shunt 106 is substantially the same as the shunt 102 of FIG. 3 except the following: A fiber bundle 20 is provided in the axial channel 121 of the shunt 106. Fluid in the front chamber of the eyeball 40 may be discharged through the fiber bundle 20 due to capillary action of the fiber bundle 20, thereby lowering eye pressure. The medicine storages 16 are adapted to direct flow if they are not blocked by medicine.

The bio-activated glass may be degraded, from inside to outside, in 24 hours, one month, six months or one to three years. The time required for degradation depends on sizes, wall thicknesses, lengths and layers of the shunts 10, 101, 102, 103, 104, 105 and 106. The bioactive silicate (e.g., bioactive glass) having different compositions or a composition of high density silica can carry out the different times of degradation. As a result, time and amount of medicine being discharged can be controlled.

The biosilicates are bioresorbable and water soluble.

While the invention has been described in terms of preferred embodiments, those skilled in the art will recognize that the invention can be practiced with modifications within the spirit and scope of the appended claims.

What is claimed is:

1. A combination bioactive silicate medicine carrier and shunt, comprising:
   a shunt made of bioactive silicate or glass adapted to be bioresorbable and water soluble, the shunt including at least one indentation disposed on an outer surface of the shunt, an axial channel, and a tapered insertion end, wherein a plurality of tunnel shaped medicine storages are equally spaced around the channel,
   wherein gaps in the bioactive silicate or gaps in the glass adapted to be bioresorbable and water soluble serve as a plurality of medicine storages for storing medicines,
   wherein the tunnel shaped medicine storages have different thicknesses, and
   wherein each of the tunnel shaped medicine storages equally spaced around the channel include at least one outer space and at least one inner space, and a plurality of dividing members each disposed between any two adjacent ones of the outer space and any two adjacent ones of the inner space, and wherein the dividing members have different thicknesses.

2. The combination bioactive silicate medicine carrier and shunt of claim 1, wherein the indentation disposed on an outer surface of the shunt comprises a plurality of groove shaped direction check member on an intermediate portion of the outer surface of the shunt.

3. The combination bioactive silicate medicine carrier and shunt of claim 1, wherein the shunt further comprises a plurality of parallel axial hollow fiber strands, wherein the fiber strands are configured so that high pressure fluid at a first end of the shunt flows to low pressure at an opposite second end of the shunt via a micro capillary effect.

4. The combination bioactive silicate medicine carrier and shunt of claim 1, wherein the tunnel shaped medicine storages are arranged in a predetermined order.

5. The combination bioactive silicate medicine carrier and shunt of claim 1, wherein the bioactive silicate is adapted to degrade, from inside to outside or outside to inside, in 24 hours, one month, six months or one to three years.

6. The combination bioactive silicate medicine carrier and shunt of claim 1, wherein the shunt is shaped as a bullet, a capsule, or an olive.

* * * * *